US011124901B2

(12) United States Patent
Sheftel et al.

(10) Patent No.: US 11,124,901 B2
(45) Date of Patent: Sep. 21, 2021

(54) COMPOSITE FABRIC, METHOD FOR FORMING COMPOSITE FABRIC, AND USE OF A COMPOSITE MATTER FABRIC

(71) Applicant: FIRST STEP HOLDINGS, LLC, Tucson, AZ (US)

(72) Inventors: Scott N. Sheftel, Tucson, AZ (US); Jeffry B. Skiba, Chandler, AZ (US); Stanley N. Sheftel, Akron, OH (US)

(73) Assignee: FIRST STEP HOLDINGS, LLC, Tucson, AZ (US)

( * ) Notice: Subject to any disclaimer, the term of this patent is extended or adjusted under 35 U.S.C. 154(b) by 0 days.

(21) Appl. No.: 15/823,076

(22) Filed: Nov. 27, 2017

(65) Prior Publication Data
US 2019/0161910 A1 May 30, 2019

(51) Int. Cl.
*D01F 1/10* (2006.01)
*D01F 8/04* (2006.01)
*D01F 6/04* (2006.01)
*D01F 6/62* (2006.01)

(52) U.S. Cl.
CPC ............... *D01F 1/10* (2013.01); *D01F 1/103* (2013.01); *D01F 6/04* (2013.01); *D01F 6/62* (2013.01); *D01F 8/04* (2013.01); *D10B 2321/021* (2013.01); *D10B 2321/08* (2013.01); *D10B 2331/04* (2013.01); *D10B 2501/02* (2013.01); *D10B 2501/041* (2013.01); *D10B 2501/043* (2013.01)

(58) Field of Classification Search
None
See application file for complete search history.

(56) References Cited

U.S. PATENT DOCUMENTS 3,655,542 A * 4/1972 Tamai ............... B29C 44/461
  521/50.5
4,425,917 A 1/1984 Kuznetz ..................... 607/110
5,445,901 A 8/1995 Korall et al. ................. 429/27
(Continued)

FOREIGN PATENT DOCUMENTS

EP 0 364 153 4/1990 ............ B01J 35/06
EP 0 510 619 10/1992 ............ A61F 13/15
(Continued)

OTHER PUBLICATIONS

Netafim, Mesh vs. Micron Comparison Chart, https://www.netafimusa.com/wp-content/uploads/2016/10/Mesh-vs-Micron.pdf, accessed on Dec. 10, 2018. (Year: 2016).*
(Continued)

*Primary Examiner* — Marla D McConnell
*Assistant Examiner* — Christine X Nisula
(74) *Attorney, Agent, or Firm* — Hayes Soloway P.C.

(57) ABSTRACT

A fiber material formed of a thermoplastic or thermosetting material containing particles of metal disbursed there through. More particularly, there is disclosed a fiber material formed of a thermoplastic or thermosetting material containing particles of metal dispersed intermittently within the fiber material during fiber formation, wherein the particles of metal are exposed at least in part on a surface of the fiber material, wherein the fiber material also includes carbon fiber nanotubes added to the fiber material, and wherein the fiber material is woven into a fabric and the fabric is formed into an article of clothing.

9 Claims, 2 Drawing Sheets

(56) References Cited

U.S. PATENT DOCUMENTS

| | | | |
|---|---|---|---|
| 5,861,044 A | 1/1999 | Crenshaw | 8/115 |
| 5,897,673 A | 4/1999 | Nishida et al. | 8/624 |
| 6,203,810 B1 | 3/2001 | Alemany et al. | 424/404 |
| 6,331,265 B1* | 12/2001 | Dupire | B29C 55/00 264/119 |
| 6,584,668 B2 | 7/2003 | Green et al. | 29/527.2 |
| 6,602,811 B1 | 8/2003 | Rock et al. | 442/312 |
| 7,457,667 B2 | 11/2008 | Skiba | 607/50 |
| 7,488,517 B2 | 2/2009 | Whang et al. | 427/412 |
| 7,662,176 B2 | 2/2010 | Skiba et al. | 607/1 |
| 7,672,719 B2 | 3/2010 | Skiba et al. | 607/2 |
| 7,813,806 B2 | 10/2010 | Skiba | 607/50 |
| 7,904,147 B2 | 3/2011 | Schneider et al. | 607/2 |
| 8,204,587 B2 | 6/2012 | Pak et al. | 604/20 |
| 8,224,439 B2 | 7/2012 | Skiba et al. | 607/2 |
| 9,192,761 B2 | 11/2015 | Sheftel et al. | A61N 1/32 |
| 9,511,215 B2 | 12/2016 | Skiba | A61N 1/0464 |
| 9,707,172 B2 | 7/2017 | Sheftel et al. | A61K 9/0009 |
| 9,731,109 B2 | 8/2017 | Skiba | A61N 1/0468 |
| 9,777,265 B2 | 10/2017 | Subramaniam et al. | C12N 13/00 |
| 9,912,761 B2 | 3/2018 | Amano | |
| D816,233 S | 4/2018 | Del Rossi | D24/189 |
| D825,766 S | 8/2018 | Del Rossi | D24/189 |
| D838,373 S | 1/2019 | Del Rossi | D24/189 |
| D846,129 S | 4/2019 | Del Rossi | D24/189 |
| 10,279,176 B1 | 5/2019 | Sheftel et al. | |
| 10,662,561 B2 | 5/2020 | Yung et al. | D04H 1/4334 |
| 10,744,351 B2 | 8/2020 | Fujimori et al. | A62B 23/025 |
| 2002/0086036 A1 | 7/2002 | Walker | 424/236.1 |
| 2003/0064222 A1 | 4/2003 | Nakamura et al. | 428/375 |
| 2003/0224684 A1 | 12/2003 | Botturi | G21F 3/02 |
| 2004/0004196 A1* | 1/2004 | DeMeo | B32B 5/26 250/516.1 |
| 2005/0010192 A1 | 1/2005 | Sun et al. | 604/501 |
| 2005/0148996 A1 | 7/2005 | Sun et al. | A61N 1/30 |
| 2006/0169284 A1 | 8/2006 | Meyer | 128/205.26 |
| 2006/0258973 A1 | 11/2006 | Volt | |
| 2007/0006358 A1 | 1/2007 | Rey | 2/53 |
| 2007/0191756 A1 | 8/2007 | Tapper | 604/20 |
| 2009/0062720 A1 | 3/2009 | Anderson et al. | |
| 2009/0171440 A1* | 7/2009 | Carlson | A61F 2/06 623/1.15 |
| 2010/0057147 A1 | 3/2010 | Fassih et al. | |
| 2010/0082088 A1 | 4/2010 | Fassih et al. | 607/149 |
| 2010/0173070 A1 | 7/2010 | Niu | 427/215 |
| 2010/0209515 A1 | 8/2010 | Chantalat et al. | 424/490 |
| 2010/0221969 A1 | 9/2010 | Chen et al. | 442/189 |
| 2011/0016637 A1 | 1/2011 | Boardman et al. | 8/137 |
| 2011/0159758 A1 | 6/2011 | Martin | 442/1 |
| 2012/0016446 A1 | 1/2012 | Panting | 607/62 |
| 2012/0064313 A1 | 3/2012 | Rock et al. | 428/212 |
| 2012/0148633 A1 | 6/2012 | Sun et al. | 424/400 |
| 2012/0164449 A1 | 6/2012 | Foss | D01D 1/02 |
| 2012/0180800 A1 | 7/2012 | Shibata | 128/863 |
| 2012/0192876 A1 | 8/2012 | Fujimori et al. | 128/863 |
| 2012/0289107 A1* | 11/2012 | Beissinger | D04H 13/00 442/1 |
| 2012/0321832 A1 | 12/2012 | Makepeace | 428/57 |
| 2013/0072406 A1* | 3/2013 | Sueda | C01G 9/00 508/170 |
| 2013/0183495 A1* | 7/2013 | Rock | D06M 11/50 428/156 |
| 2013/0239298 A1 | 9/2013 | Jordan | 2/250 |
| 2014/0066872 A1 | 3/2014 | Baer | 604/367 |
| 2014/0261459 A1 | 9/2014 | Santelli | 128/858 |
| 2014/0308504 A1 | 10/2014 | Son | D01F 1/106 |
| 2015/0143601 A1 | 5/2015 | Longinotti-Buitoni et al. | A41D 1/002 |
| 2015/0182473 A1* | 7/2015 | Bosnyak | A61K 9/703 514/356 |
| 2016/0008273 A1* | 1/2016 | Sheftel | A61K 9/0009 424/402 |
| 2016/0024699 A1* | 1/2016 | Aldridge | G01V 3/38 442/337 |
| 2016/0115630 A1* | 4/2016 | Kubota | D01D 5/32 442/353 |
| 2016/0174631 A1 | 6/2016 | Tong | 128/863 |
| 2017/0087350 A1 | 3/2017 | Skiba | A61N 1/0468 |
| 2017/0106188 A1 | 4/2017 | King et al. | A61N 1/328 |
| 2017/0113038 A1 | 4/2017 | Nagel et al. | A61N 1/36014 |
| 2017/0128720 A1 | 5/2017 | Skiba | A61N 1/326 |
| 2017/0173372 A1 | 6/2017 | Bischof et al. | |
| 2017/0226688 A1 | 8/2017 | Komarov | |
| 2017/0274228 A1 | 9/2017 | Nguyen | |
| 2017/0367416 A1 | 12/2017 | Yamada | |
| 2018/0243674 A1 | 8/2018 | Gulrez | |
| 2018/0338866 A1 | 11/2018 | Kharazmi | |
| 2019/0275454 A1 | 9/2019 | Wendland | |
| 2020/0085124 A1 | 3/2020 | Chiang | |
| 2020/0179903 A1 | 6/2020 | Beiermann | |
| 2020/0187494 A1 | 6/2020 | Osborn et al. | A01N 25/10 |
| 2020/0254371 A1 | 8/2020 | Yung et al. | B01D 39/163 |
| 2020/0283937 A1 | 9/2020 | Yung et al. | D04H 1/4334 |

FOREIGN PATENT DOCUMENTS

| | | | |
|---|---|---|---|
| WO | WO 02/091977 | 11/2002 | A61F 13/84 |
| WO | WO2010027792 | 3/2010 | A61N 1/20 |
| WO | WO 2012/143576 | 10/2012 | A61K 31/12 |
| WO | WO-2015187858 A1 * | 12/2015 | A61N 1/205 |

OTHER PUBLICATIONS

San Diego Plastics, http://www.sdplastics.com/polyeth.html., accessed on Nov. 26, 2019. (Year: 2019).*

Endenburg, "Polyester", accessed on Nov. 26, 2019. (Year: 2019).*

Percentage by Weight to Percentage by Volume Conversion Calculator, https://handymath.com/cgi-bin/dnstywtvol.cgi?submit=Entry , accessed on Nov. 26, 2019. (Year: 2019).*

Camel et al., "The Effect of Saline Iontophoresis on Skin Integrity in Human Volunteers," Fundamental and Applied Toxicology 32, 168-178 (1996) (11 pgs).

Guffey et al., "Skin pH changes associated with iontophoresis," J Orthop Sports Phys Ther., Nov. 1999; 29(11):656-60 (2 pgs).

Li et al., "A Method for Measuring the Volume of Transdermally Extracted Interstitial Fluid by a Three-Electrode Skin Resistance Sensor," Sensors, 2014, 14, 7084-7095 (12 pgs).

Notice of Allowance issued in U.S. Appl. No. 14/213,735, dated Jul. 24, 2015 (7 pgs).

Notice of Allowance issued in U.S. Appl. No. 14/864,541, dated Oct. 25, 2016 (10 pgs).

Office Action issued in U.S. Appl. No. 14/213,735, dated Apr. 17, 2015 (6 pgs).

Anonymous, "Micro Current Technology," downloaded Feb. 10, 2015 from http://www.bio-therapeutic.in/micro-current-technology.php (5 pgs).

Anonymous, "Microcurrent Stimulation and Microcurrent Therapy," downloaded Feb. 10, 2015, from http://www.microcurrentsystems.com ) (5 pgs).

Anonymous, "Ohm's Law (again!)," Electrical Safety-Electronics Textbook, downloaded Mar. 8, 2015 from http://www.allaboutcircuits.com/vol_1/chpt-3/4.html(6 pgs).

Bagherani et al., "An overview of zinc and its importance in dermatology—Part II: The association of zinc with some dermatologic disorders", Separtment of Dermatology, University of Rochester, School of Medicine and Dentistry USA, Glob Dermatol, 2016, vol. 5(5), pp. 337-350.

Bogie et al., "Effects of regular use of neuromuscular electrical stimulation on tissue health," Journal of Rehabilitation Research and Development. vol. 40, No. 6, Nov./Dec. 2003, pp. 469-476 (7 pgs).

Bolton et al., "Direct-Current Bactericidal Effect on Intact Skin," Antimicrobial Agents and Chemotherapy, Jul. 1980, pp. 137-141 (5 pgs).

Bruning, Elizabeth, "A new topical product form featuring biomimetic electrical signaling generated by a zinc-copper galvanic couple

(56) References Cited

OTHER PUBLICATIONS improves the signs of clinical photoaging in a 12-week placebo-controlled study", Journal of the American Academy of Dermatology, vol. 66, issue 4, Supplement 1, p. AB31.
Carter et al., "Electric current flow through human skin at power frequency voltages," Brit. J. Industr. Med., 1969, 26, pp. 217-233 (7 pgs).
Chandak et al., "Modern Homeopathy An evidence based information on Homoeopathy," website: http://www.modernhomeopathy.com/anndt%20law.htm as of Oct. 8, 2015 (2 pgs).
Cheng et al., "The Effects of Electric Currents on ATP Generation, Protein Synthesis, and Membrane Transport in Rat Skin," Clinical Orthopaedics and Related Research, 171, (Nov.-Dec. 1982) pp. 264-272 (9 pgs).
Cole, K.S., "Electrical Conductance of Biological Systems," Cold Spring Harbor Symposia on Quantitative Biology, 1933, 1:107-116 (excerpt only) (1 pg).
Fish et al., *Medical and Bioengineering Aspects of Electrical Injuries*, Lawyers & Judges Publishing Company, 2003, book overview (13 pgs).
Giudice, "Reinforcement Fibers in Zinc-Rich Nano Lithiun Silicate Anticorrosive Coatings", UTN (Universidad Technologica Nacional), Chapter 7, www.intechopen.com; 2012.
Gupta et al., "Zinc Therapy in Dermatology: A Review"; Department of Dermatology, Venereology & Leprosy, Hindawi Publishing Corporation; vol. 2014, Article IDS 709152, 11 pages, Published Jul. 10, 2014.
International Search Report issued in application No. PCT/US2014/029239, dated Sep. 24, 2015 (8 pgs).
International Search Report issued in application No. PCT/US2014/029239, dated Jul. 7, 2014 (12 pgs).
Kirsch et al., "Electromedicine: The Other Side of Physiology," Innovations in Pain Management: A Practical Guide for Clinicians (6th ed.) Boca Raton, Fla., 2002, American Academy of Pain Management, CRC Press, pp. 749-758 (14 pgs).
Ladizinsky, et al., "New Insights Into Oxygen Therapy for Wound Healing," Wounds, 2010, vol. 22, No. 12, pp. 294-300. (11 pgs).
Lambert et al., "Electro-membrane microcurrent therapy reduces signs and symptoms of muscle damage," Medicine & Science in Sports & Exercise, 2002, vol. 34, No. 4, pp. 602-607 (6 pgs).
Ma et al., "Extraordinarily High Conductivity of Stretchable Fiberts of Polyurethane and Silver Nanoflowers", ACS Nano, 2015, 9(11), pp. 10876-10886.
Madehow.com, "Polyester"; vol. 2; accessed Oct. 3, 2017; http://www.madehow.com/Volume-2/Polyester.html.
McMakin, C., "Microcurrent therapy: a novel treatment method for chronic low back myofascial pain," Journal of Bodywork and Movement Therapies, 2004, 8, pp. 143-153 (11 pgs).
Miscellaneous, "Doctors' Comments," downloaded Oct. 8, 2015 from http://www.drionics.com (5 pgs).
Muirhead, "Antibacterial Ointments Versus Petrolatum-Based Ointments in Clean Wounds for Wound Healing", Pacific University CommonKnowledge, School of Physician Assistant Studies, Theses, Dissertations and Capstone Products; Aug. 11, 2012.
Nuttall et al., "Zinc and the aging brain", Genes Nutr (2014) 9:379, Jul. 16, 2013.
Office Action issued in U.S. Appl. No. 14/213,735, dated Feb. 3, 2015 (10 pgs).
Office Action issued in U.S. Appl. No. 14/213,735, dated Jun. 19, 2015 (7 pgs).
Office Action issued in U.S. Appl. No. 14/213,735, dated Oct. 7, 2014 (13 pgs).
Office Action issued in U.S. Appl. No. 14/864,541, dated Jun. 6, 2016 (25 pgs).
Park et al., "The Effect of Microcurrent Electrical Stimulation on the Foot Blood Circulation and Pain of Diabetic Neuropathy," Journal of Physical Therapy Science, 2011, vol. 23, No. 3, pp. 515-518 (4 pgs).
Pfeiffer, E.A., "Electrical stimulation of sensory nerves with skin electrodes for research, diagnosis, communication and behavioral conditioning: a survey," Medical Biological Engineering, 1968, vol. 6, issue 6, pp. 637-651 (7 pgs).
Poltawski et al., Bioelectricity and microcurrent therapy for tissue healing—a narrative review, Physical Therapy Reviews, 2009, vol. 14, No. 2, pp. 105-114 (9 pgs).
Richter, C.P., "Physiological factors involved in the electrical resistance of the skin," American Journal of Physiology. vol. 88, 1929, pp. 596-615 (abstract only) (1 pg).
Rowlerson et al., "The fibre-type composition of the first branchial arch muscles in carnivore and primates," Journal of Muscle Research & Cell Motility Aug. 1983, vol. 4, issue 4, pp. 443-472 (5 pgs).
Shanmuganathan et al., "Highly Stretchable Thermoset Fibers and Nonwovens Using Thiol-ene Photopolymerization", ACS Applied Materials and Interfaces, 2014 6(16) pp. 14259-14265.
Suzuki, D., "The Body Electric," Skin Inc., Oct. 2007, downloaded from http://www.skininccom/skinscience/physiology/17969919.html (6 pgs).
Wang, W., "Oxygen partial pressure in outer layers of skin: simulation using three-dimensional multilayered models," Microcirculation, Mar. 2005, vol. 12, No. 2, pp. 195-207 (abstract only) (2 pgs).
Wikipedia, Heatsetting; accessed Oct. 3, 2017, https://en.wikipedia.org/wiki/heatsetting.
Wikipedia, Nonwoven fabric; accessed Oct. 2, 2017, https://en.wikipedia.org/wiki/nonwoven_fabric.
Wikipedia, Metal-Air electrochemical cell; accessed Oct. 2, 2017, https://en.wikipedia.org/wiki/metal%E2%80%93_air_electrochemical_cell.
International Search Report issued in PCT Appln. No. PCT/US2018/062634, dated Feb. 7, 2019, 9 pages.
Choi, Charles Q. "These 3 Electroceuticals Could Help You Heal Faster" IEEE Spectrum, Jan. 25, 2019, 4 pages.
"Prosit™: A Novel Bioelectric Dressing", Silverleaf Medical Products, Inc., Jun. 2008, 8 pgs.
Sheftel, Scott "Wound Healing Initiation through Bioelectric Wound Care Technology" Poster at AAWC Research Committee, Apr. 2010, 3 pgs.
"Bioelectric Dressings Initiate Healing in Acute and Chrnoic Wounds: A Case Series" Dec. 2008, 11 pgs.
Gardner, Sue et al., "Effect of electrical stimulation on chronic wound healing: a meta-analysis" *The Wound Healing Society*, Wound Repair and Regeneration, Nov.-Dec. 1999, 9 pgs.
"Bio-electrical stimulation therapy using PROiFECT® RD", Wounds UK, 2006, vol. 2, No. 4, 4 pgs.
Kloth, LC "Electrical stimulation for wound healing: a review of evidence from in vitro studies, animal experiments, and clinical trials." *International Journal Lower Extremities Wounds*, Mar. 2005; 4(1), abstract only, 1 page.
"Ivivi PEMF Technology Accelerates Wound Healing in Laboratory Animals, Study Reports" Business Wire, Jul. 23, 2007, 2 pgs.
Kwan et al., "Efficacy of Biophysical Energies on Healing of Diabetic Skin Wounds in Cell Studies and Animal Experimental Models: A Systematic Review" *International Journal of Molecular Sciences* 2019, 20, 368, 38 pgs.
"Electrical Fields, Microcurrents and Their Essential Role in Human Tissue Regeneration" Vomaris, Presentation May 1, 2014, 35 pgs.
"Introduction to Procellera® Technology" Vomaris, Presentation 2016, 64 pgs.
U.S. Appl. No. 16/005,436, filed Jun. 11, 2018.
International Preliminary Report on Patentability issued in PCT Appln. No. PCT/US2018/062634, dated Jun. 11, 2020, 6 pages.
U.S. Appl. No. 14/213,735, filed Mar. 14, 2014.
U.S. Appl. No. 14/864,541, filed Sep. 24, 2015.
U.S. Appl. No. 16/952,938, filed Nov. 19, 2020.
U.S. Appl. No. 17/073,261, filed Oct. 16, 2020.
U.S. Appl. No. 17/110,093, filed Dec. 2, 2020.
U.S. Appl. No. 16/952,938, filed Nov. 19, 2020, Skiba et al.
U.S. Appl. No. 17/073,261, filed Oct. 16, 2020, Skiba et al.
U.S. Appl. No. 17/110,093, filed Dec. 2, 2020, Skiba et al.
Ali, Attarad, et al., "Elemental zinc to zinc nanoparticles: is ZnO NPs crucial for life? Synthesis, toxicological and environmental concerns", Nanotechnol Rev 2018; 7(5), pp. 413-441.

(56) References Cited

OTHER PUBLICATIONS

Aznan, Nurual Azri, et al., "Quantum Size Effect in ZnO Nanoparticles via Mechanical Milling", Advanced Materials Research Laboratory, Journal of Nanomaterials, vol. 2012, Article IDS 439010, (4 pages), Sep. 16, 2011.
Taylor-Smith, Kerry, "An Introduction to the Quantum Mechanics of Nanoparticles", An Introduction to Quantum Mechanics of Nanoparticles, Feb. 5, 2020, https://www.azoquantum.com/Article/aspx?ArticleIDS=179.
Jiang et al., "The advancing of zinc oxide nanoparticles for Biomedical Applications", Bioinorganic Chemistry and Applications, vol. 2018, 18 pages.
Office Action issued in U.S. Appl. No. 16/941,371, dated Nov. 25, 2020 (22 pgs).
Rasmussen et al., "Zinc Oxide Nanoparticles for Selective Destruction of Tumor", Expert Opin Drug Deliv, Sep. 2010; 7(9), pp. 1063-1077.
Office Action issued in U.S. Appl. No. 16/941,371, dated Mar. 15, 2021 (22 pgs).
Office Action issued in U.S. Appl. No. 16/952,938, dated Feb. 18, 2021 (29 pgs).
International Search Report and Written Opinion issued in PCT International Patent Application Serial No. PCT/US19/36123, dated Dec. 19, 2019 (7 pgs).
International Preliminary Report on Patentability issued in PCT International Patent Application Serial No. PCT/US19/36123, dated Dec. 15, 2020 (5 pgs).
Office Action issued in U.S. Appl. No. 16/005,436, dated Sep. 24, 2018 (19 pgs).
Simple Respiratory Mask, Centers for Disease Control and Prevention, EID Journal, vol. 12, No. 6, Jun. 2006.
Yahoo!News, "ION Manufacturing Unveils ZnTech: A Revolutionary Zinc Fiber Microcurrent That Kills Coronavirus", Oct. 9, 2020.
"3G Med Supplies" https://www.3gmed.co.th/, 2019, 1 pg.
Ambu website, https://www.ambuusa.com/, 2019, 5 pgs.
Brown II, Don E. MSIS "Bioelectricity, Qi, and the Human Body", Mindful Life by Design School of Chi Energy Heals, www.chienergyheals.com, Jan. 13, 2015, 3 pgs.
"How to Increase Bioelectricity" PHILCAT BIOFLOW, https://philcatbioflow.com/how-to-increase-bioelectricity/, Apr. 13, 2019, 8 pgs.
"How Your Body Voltage Dictates Health and Disease" Condensed by Dr. Mercola, New Health Options: A Private Membership Association, http://www.newhealthoptions.org/?page_id=2402, date unknown, 7 pgs.
Kloth, Luther C. "Electrical Stimulation Technologies for Wound Healing" Advances in Wound Care, vol. 3, No. 2, pp. 81-90, 2014, 10 pgs.
Lepine, Eugenio, "The Electromagnetic Human Field" *Human Frequencies*, https://www.humanfrequencies.com/electromagnetic-human-field/, 2016, 14 pgs.
Matchar, Emily "Tweaking the Tiny Electrical Charges Inside Cells Can Fight Infection" Smithsonian.com https://smithsonianmag.com/innovation/using-bodys-own-electricity-fight-infection-180963460/#56p3jdzP55P6iTls.99 May 26, 2017, 3 pgs.
"Procellera™ Antimicrobial Wound Dressing" Ambu USA https://webcache.googleusercontent.com/search?q=cache:_16RNxrPSggJ:https://www.ambuusa.com/products/anesthesia/regional-anesthesia/product/procellera-antimicrobial-wound-dressing+&cd=6&hl=en&ct=clnk&gl=us, website not dated, 5 pgs.
Schaefer, Katie "J&J Researchers Stimulate Skin's Bioelectricity with Microparticle Minerals" Cosmetics & Toiletries, https://www.cosmeticsandtoiletries.com/formulating/category/antiaging/87113862.html, Mar. 9, 2010, 2pgs.
"The Science of Bioelectricity" E-QURE Electric Quick Ulcer Remedy, http://www.e-qure.com/the-science-of-bioelectricity/the-science-of-bioelectricity, 2012, 3 pgs.
"Sentinel Studies Find New Microcurrent Generating Wound Dressing Effective in Disrupting Bacterial Biofilms" Thailand News Gazette, Apr. 6, 2015 https://www.thailandnewsgazette.com/sentinel-studies-find-new-microcurrent-generating-wound-dressing-effective-in-disrupting-bacterial-biofilms/ 8 pgs.
https://www.vomaris.com/products/procellera/ Procellera by Vomaris Wound Care, Inc., 5 pgs.
Wahlsten, O. et al. "Electrical field landscape of two electroceuticals" *Journal of Electrical Bioimpedance*, vol. 7, pp. 13-19, May 27, 2016, 7 pgs.
Invitation to Pay Additional Fees issued in related PCT International Patent Application Serial No. PCT/US2021/028238, dated Jun. 24, 2021 (2 pages).
Office Action issued in U.S. Appl. No. 16/952,938, dated Jun. 11, 2021 (27 pgs).
Office Action issued in U.S. Appl. No. 17/073,261, dated Jun. 25, 2021 (26 pgs).
Office Action issued in U.S. Appl. No. 17/110,093, dated Jun. 25, 2021 (33 pgs).

\* cited by examiner

COMPOSITE FABRIC, METHOD FOR FORMING COMPOSITE FABRIC, AND USE OF A COMPOSITE MATTER FABRIC

BACKGROUND OF THE INVENTION

Living tissue has inherent electrical nature that includes the creation of voltage, current, capacitance and impedence. The external application of electrical energy to any biological tissue may have therapeutic effects if the delivery method is safe and at an appropriate physiological level. In a human body, electrical charges around a cell may open voltage dependent gates, allowing cellular cytoplasm to contact the extracellular environment. The infinite combinations of voltage, current, capacitance and impedence are employed within living tissue as a foundation of life. However, an understanding of the nature of living state electrical energy is elusive since measurement of energy in the nano and pico volts/ampere range has been confined to a relatively small area of physics. Muscles are activated by electrical action potentials contained within an insulated nerve bundle. External stimuli is converted into electrical impulses stored in the brain and sent down the nerve bundles. In a cellular matrix, the extracellular fluid acts as a conductor and functions independently of the muscle action signals. Afferent and efferent nerves send signals back and forth to the brain in a similar manner, through insulated nerves.

The recent development of smart fabrics that can provide an electrical field over the skin for stimulus, to measure impedence, warm the user and/or provide feedback about the users' health represent novel devices specifically aimed at a physiologic function. By way of example, our earlier U.S. Pat. Nos. 9,192,761 and 9,707,172 describe methods and devices for treating various conditions including hyperhidrosis and other conditions such aas neuropathic pain including peripheral artery disease and neuropathy; surgical rehabilitation and surgical convalescence including joint surgery rehabilitation and soft tissue healing; and physical therapy including muscle and tendon healing and stroke rehabilitation, by applying onto a skin surface of a patient in need of said treatment, a device comprising a fabric or substrate containing elemental zinc particles arranged so that the fabric or substrate forms a plurality of half-cells of an air-zinc battery, whereby to produce an ion exchange with the skin of the patient. Zinc or zinc salt against the skin will result in secondary reactions to form zinc complexes beneficial to the host. The ability to deliver topical zinc to the surface of the skin can have beneficial effects provided the topical zinc is in the correct quantity.

Additionally, the therapeutic value of metals and metal salts such as zinc, zinc oxide and zinc salt in cosmetic and medicinal ointments and creams, i.e., for treating a variety of skin conditions is well documented in the art. However, one of the limitations of creams or ointments is that they require a carrier gel or petrolatum, and these carriers create barriers on the skin, potentially trapping microbes beneath the barriers. Confirmatory studies are required to assure that these creams and ointments are effective in preventing colonization of bacterial strains and resultant biofilms forms of the bacteria, significantly increasing the challenge of any antimicrobial to function.

It has been postulated that many of the same benefits of direct application to the skin of creams or ointments containing zinc may be achieved by bringing a fabric having elemental zinc particles printed thereon, in contact with the skin of the patient, i.e., as described in our aforesaid '761 and '172 patents. However, fabric coated with elemental zinc particles as described above formed by printing zinc particles on the surface of the fabric have limited washability and abrasion resistance. Also, in the case of thermoplastics, once they exceed about 30% solids in the melt, the strength of the fiber drops considerably. There are many thermosetting and thermoplastic polymers as well as other "binders" such as printer's ink, silicone, natural collagen or cellulose binders that could be used to suspend the metal powder (or salt thereof) or combination of metals within the fiber, thread or yarn. However, prior to the present invention, no one has successfully produced metal-filled fabrics having good washability and abrasion resistance.

OBJECTS OF THE INVENTION

It is therefore an object of the present invention to provide a method for producing metal-filled fabrics, i.e., fabrics having elemental zinc particles or other elemental metal particles, as well as oxides and salts of such metals or combinations of metals with other chemicals carried in or on a fabric, to fabrics so produced, and to methods for treating various conditions using the so produced fabrics.

SUMMARY THE INVENTION

In one aspect the present invention provides a method for producing metal particle filled fibers and to metal particle filled fibers produced by the method.

In another and preferred aspect, the metal particles include zinc particles, zinc oxide particles, or zinc salt particles.

In another and preferred aspect, the metal particles have a particle size range of 1 microns 200 microns, more preferably 2-100 microns, even more preferably 2-10 microns. In which cases, the metal particles preferably have an average particle size of less than about 10 microns, more preferably less than about 6 microns, even more preferably less than about 5 microns. The reason for these limitations are purely practical since the fiber spinnarettes will plug up if the particles are too large or if they clump together. In addition, if there is too much tiller compared to polymer, the fiber will weaken. We could add reinforcing carbon fiber nanotubes to increase the polymer tensile strength but doing so takes up space in the polymer that we would prefer to fill with the metal.

In still another aspect, the metal particles preferably comprise about 50% by volume, of the fiber, more preferably about 40-60 volume % of the fiber, even more preferably between about 20-30 volume % of the fiber.

In yet another aspect of the invention, the metal particles are dispersed as micro pellets within the fiber material.

In yet another aspect, the metal particle filled fiber material is formed by dispersing metal particles throughout die fiber during fiber formation.

In yet another aspect of the invention, the metal particle containing fiber is formed by mixing the metal particles with a thermosetting plastic material such as a polyester resin or a vinyl ester resin and forming the mixture as elongate fibers or threads as it sets. Alternatively, the metal particles can be dusted onto the setting fibers or threads.

In yet another aspect of the invention, the metal particle containing fiber is formed by spinning, drawing or extruding a heated thermoplastic material such as a polyolefin such as polyethylene or polypropylene, or a polyamide such as nylon, or an acrylic, containing the metal particles.

The amount of metal available per fiber can be manipulated to increase/decrease concentration and spacing of reservoirs of the metal within the fiber. Metal availability also may be controlled by particle size or particle size distribution. Very fine particles may become coated with binder more than larger particles. However, the binder can be manipulated to expose more of the particle to the contact area. By controlling the particle size, performance of the fiber will differ.

The amount of metal available per thread or yarn also can be manipulated to increase/decrease concentration and spacing of reservoirs of the metal within the thread or yarn. This may be done at the fiber level by adjusting the amount of metal held within the fiber and how the metal is attached to the fiber. We can fill the fiber with a large amount or a small amount of metal, or we can co-extrude metal filled fiber over another fiber so the only part of the fiber loaded with metal is the outer wrap. We also can manipulate the extrusion to create pockets of high and low metal concentrations, or no metal at all.

In the case of a monofilament we can "bump extrude" the filament with metal to produce thicker portions of metal filled filament and thinner portions created by the frequency of the "bumps".

By controlling the amount and particle size of metals in the fiber and how the metal is bound to the fiber, we can adjust slow or fast release of ions. We also can increase or decrease the reservoir capacity within the fiber and subsequently the capacity of the battery created when combined with oxygen

BRIEF OF THE DRAWINGS

Further features and advantages of the present invention will be seen from the following detailed description, taken in conjunction with the accompanying drawings, Wherein like numerals depict like parts, and wherein.

DETAILED DESCRIPTION OF THE INVENTION

In the following description, the term "metal particles" may include elemental metal particles of metals capable of forming metal-air electrochemical cells, and oxides and salts thereof. Preferred are zinc metal particles and oxides and salts thereof, although other metals and oxides and salts thereof may be used including aluminum, iron, copper, or magnesium.

The term "fibers" may comprise both natural and synthetic fibers, filaments and threads, although synthetic fibers are preferred, in particular, fibers formed of thermoplastic or thermosetting plastic materials.

As used herein "metal filled fibers" means fibers, having metal particles carried on or within the fibers, and in which the metal particles are at least in part exposed to air.

The present invention provides a method for forming metal particle filled fibers suitable for weaving or knitting into cloth for use in treating hyperhidrosis or neuropathy, or other conditions according to our prior '761 and '172 patents, and other conditions as above discussed. More particularly, the present invention provides a method for producing metal particle containing fibers that are capable of standing up to washing (at least 20 washes) abrasion resistance, and have the ability to release ions when in contact with a patient's skin.

Figure 1:
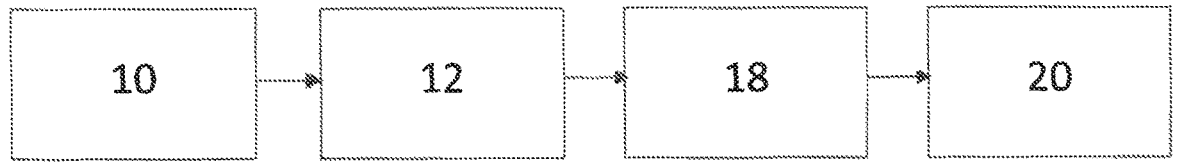
FIG. 1 is a flow diagram showing one method for forming a metal particle filled fiber in accordance with the present invention.
Figure 4:
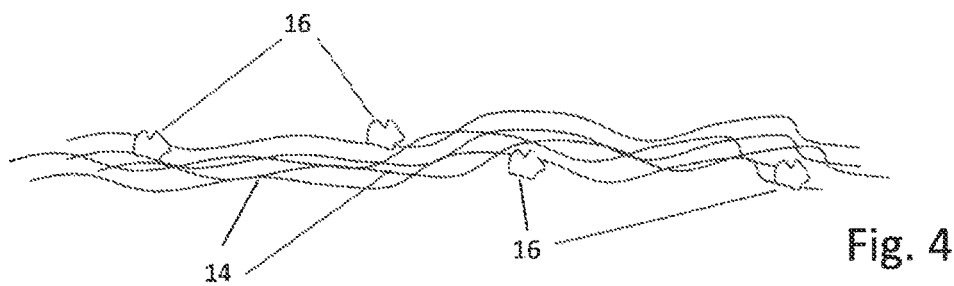
FIG. 4 is a side elevational view of a metal particle filled fiber made in accordance with the present invention.
Figure 3:
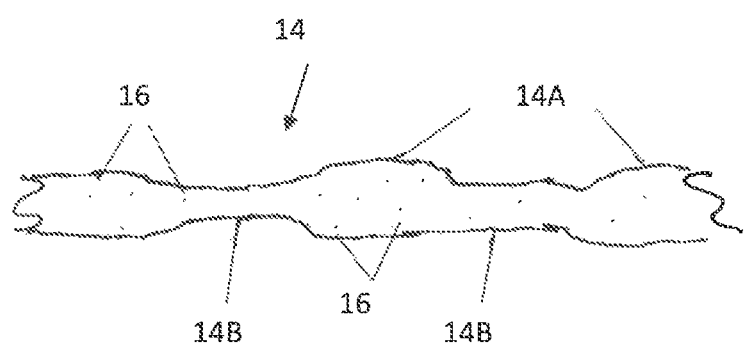
FIG. 3 is a side elevational view of a monofilaments fiber made in accordance with the present invention.

Referring to FIG. 1, according to a first embodiment of our invention, metal particles, typically metallic zinc particles which may be previously formed by grinding or precipitated out of suspension, and having an average particle size between 1 and 100 nanometers, more preferably 1-10 microns, even more preferably about 5 microns are mixed with a thermoplastic material such as polyethylene in a heated mixing vat 10 to melt the material, and the mixture bump extruded or melt spun at spinning station 12 to form fibers 14, having thicker portions 14A of metal particles 16 filled filaments and thinner portions 14B of metal particles 16 filled filaments therebetween (see FIGS. 3 and 4). The polyethylene is the polymer of choice for releasing of electrons from the metal. The porosity of the fiber also is believed to play a part. Polyacrylie or polyester fibers also may be used; however the result is a slower ion release. The metal particles filled fibers may then be cabled or twisted at a cabling station 18, and woven at a weaving or knitting station 20 into a garment such a sock, underwear, shirt, or a cloth which may be made into a therapeutic wrap (see FIG. 5) for use in treating hyperhidrosis, neuropathy and other condition as described in our aforesaid '761 and '172 patents.

Figure 2:
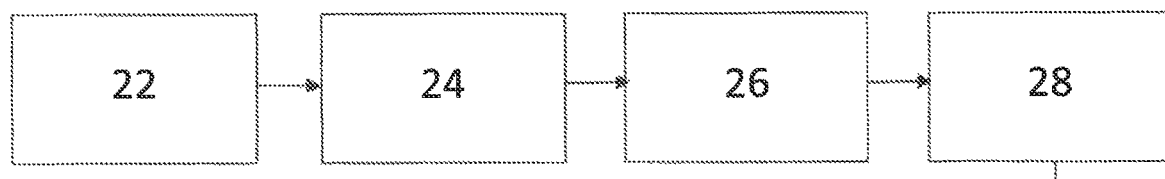
FIG. 2 is a flow diagram showing an alternative method for forming a metal particle filled fiber in accordance with the present invention.

Referring to FIG. 2, according to a second embodiment of the invention, metal particles, typically metallic zinc particles having an average particle size between 1 and 100 microns, preferably 1-10 microns, even more preferably about 5 microns are mixed with a thermosetting polymer material such as polyester chips in a melting vat 22. The molten mixture is expressed through a spinneret at station 24 to form an elongate thread having metal particles incorporated into the thread with the metal particles exposed at least in part on the surface of the thread. Alternatively, pure polyester chips may be spun or pulled from the melt, and dusted with metal particle as the thread sets. The thread is then cabled or twisted at a cabling station 26, woven into cloth at a weaving station 28, and the cloth formed into an article of clothing or wrap at step 30.

Figure 5:
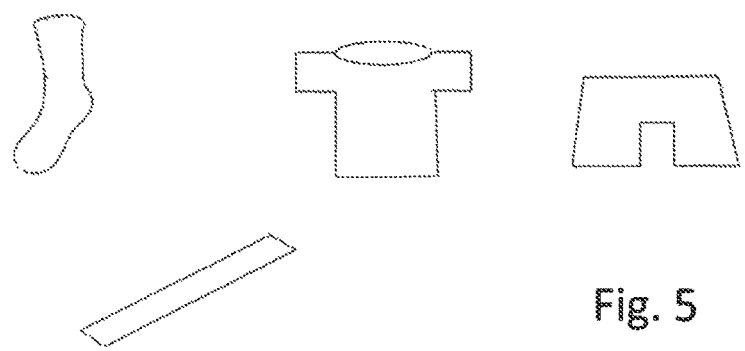
FIG. 5 is a plan view showing various articles of clothing and wraps made in accordance with the present invention.

FIG. 5 shows various examples of clothing items and wraps made in accordance with the present invention including socks, underwear, T-Shirts, wraps, etc.

Various changes may be made in the above invention without departing from the spirit and scope. For example, the fibers may be co-extruded to have a center or core of the same or dissimilar polymer with the metal filled Polymer on the outside of the fiber. Or, the metal filled polymer may be intermittently dispersed into discrete reservoirs within the fiber during fiber formation. And, we can overcome prior art limitations of fiber manufacturing with the addition of carbon fiber-nanotubes (hollow-tubes) that can provide increased tensile strength as well as the antimicrobial nature of the hollow tubes. In addition we can add prior to fiber manufacturing additives such as carbon fiber nanotubes carrying drugs to target specific cells within the host. These fibers, once spun into threads or yarns and manufactured in to a fabric will contact the target tissue closely. Also, the amount of metal particles in the fibers may be adjusted to adjust the capacity or voltage of the air battery in the thread or yarn.

The invention claimed is:

1. An article of clothing formed of a fabric material formed of woven or knitted polyethylene fibers containing particles of metal and carbon fiber nanotubes dispersed within the polyethylene fibers during fiber formation, wherein the particles of metal are selected from the group consisting of elemental zinc particles and zinc oxide particles, wherein the particles of metal have a size range of 1-200 microns, and wherein the particles of metal comprise 50-60 volume % of the polyethylene fibers, and are exposed at least in part on a surface of the polyethylene fibers, wherein the fabric material is formed by co-extruding the polyethylene fibers with a core fiber formed of a different thermoplastic material or with a thermosetting material, wherein the article of clothing is in direct contact with the skin of a wearer, at least in part, when worn, wherein the particles of metal are arranged to release ions, and wherein the article of clothing is selected from a group consisting of socks, gloves, T-shirts and underwear.

2. The articles of clothing of claim 1, wherein the particles of metal have a particle size range of 1-100 microns.

3. The article of clothing of claim 1, wherein the fabric material comprises polyethylene fiber sections containing the particles of metal and polyethylene fiber sections devoid of particles of metal.

4. The article of clothing of claim 1, wherein the fabric material further includes a drug carried by/on the carbon fiber nanotubes.

5. The article of clothing of claim 1, wherein the particles of metal have a particle size range of 2-100 microns.

6. The article of clothing of claim 1, wherein the particles of metal have a particle size range of 2-10 microns.

7. The article of clothing of claim 2, wherein the particles of metal have a particle size range of 1-10 microns.

8. The article of clothing of claim 2, wherein the particles of metal have a particle size range of 5-6 microns.

9. The article of clothing of claim 1, wherein the fabric material is capable of standing up to at least 20 washes.

\* \* \* \* \*